(12) United States Patent
Temple et al.

(10) Patent No.: US 9,050,111 B1
(45) Date of Patent: Jun. 9, 2015

(54) FENESTRATED BONE GRAFT

(71) Applicant: Vivex Biomedical, Inc., Marietta, GA (US)

(72) Inventors: Harry Thomas Temple, Miami, FL (US); Tracy Scott Anderson, Atlanta, GA (US); Edgar S. Maldonado, Pompano Beach, FL (US); Sonya A. Cooper, Miami, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 0 days.

(21) Appl. No.: 14/556,492

(22) Filed: Dec. 1, 2014

(51) Int. Cl.
- *A61F 2/28* (2006.01)
- *A61B 17/16* (2006.01)
- *A61F 2/44* (2006.01)

(52) U.S. Cl.
CPC ............... *A61B 17/1635* (2013.01); *A61F 2/28* (2013.01)

(58) Field of Classification Search
CPC ......... A61F 2/44; A61F 2/441; A61F 2/4435; A61F 2002/2828; A61F 2002/2835; A61F 2002/4475; A61F 2002/4495; A61F 2/28
See application file for complete search history.

(56) References Cited

U.S. PATENT DOCUMENTS 6,290,718 B1 * 9/2001 Grooms et al. ............... 623/1.15
2007/0233174 A1 * 10/2007 Hocking et al. ............... 606/200

OTHER PUBLICATIONS

Theodore Malinin M.D., H. Thomas Temple M.D. and Arun Garg DMD, "Bone Allografts in Dentistry: A Review".
Carpenter, Ellen M; Gendler, EI; Malinin, Theodore I; Temple, H. Thomas; "Effect of Hydrogen Peroxide on Osteoinduction by Demineralized Bone"; The American Journal of Orthopedics, 2006; 35 912 0562-567; Copyright 2006, Quadrant HealthCom Inc.
Temple, H. Thomas; Malinin, Theodore I; "Microparticulate Cortical Allograft: An Alternative to Autograft in the Treatment of Osseous Defects"; The Open Orthopaedics Journal, 2008, 2, 91-96.

* cited by examiner

*Primary Examiner* — Bruce E Snow
(74) *Attorney, Agent, or Firm* — David L. King

(57) ABSTRACT

The present invention relates to a fenestrated bone graft and a method of preparing cortical bone in thin strips then fully demineralizing it to give it formed flexibility and then creating fenestrations in the cortical bone in a fashion similar to but not identical to skin grafts.

11 Claims, 5 Drawing Sheets

FENESTRATED BONE GRAFT

TECHNICAL FIELD

The present invention relates to a fenestrated bone graft and a method of preparing cortical bone in thin strips then fully demineralizing it to give it formed flexibility and then creating fenestrations in the cortical bone in a fashion similar to but not identical to skin grafts.

BACKGROUND OF THE INVENTION

A bone graft is a surgical procedure used to fix problems associated with bones or joints. Bone grafting or transplanting of bone tissue is beneficial in fixing bones after trauma, degenerative damage, problem joints, or growing bone around implanted devices, such as total knee replacement or spinal implants. The bone used in a bone graft can come from the patient, from a donor, or could be entirely manmade. Once accepted by the patient, the bone graft provides a framework where new, living bone can grow. The two most common types of bone grafts are allograft: this graft uses bone from a deceased donor or a cadaver that has been cleaned and stored in a tissue bank and autograft: graft made from a bone inside a patient's body, such as the ribs or hips. The type of graft used depends on the type of injury the surgeon will be repairing. Allografts are commonly used in hip, knee, or long bone (arms or legs) reconstruction. The advantages are that (a) there's no additional surgery needed to acquire the bone, and (b) it lowers the risk of infection since additional incisions or surgery on the recipient will not be required. Bone grafting is done for numerous reasons, including injury and disease. There are four main reasons bone grafts are used: fractures, a bone graft may be used in the case of multiple or complex fractures or those that do not heal well after an initial treatment; fusion, most often done in the spine, fusion helps two bones heal together across a diseased joint; regeneration, used for bone lost to disease, infection, or injury, this can involve using small amounts in bone cavities or large sections of bones; and implanted devices, a graft can be used to help bone heal around surgically implanted devices, like joint replacements, plates, or screws.

All surgical procedures involve risks of bleeding, infection, and reactions to anesthesia. Bone grafts carry these and other risks, including: pain, nerve injury, rejection of the bone graft and inflammation. The surgeon typically will make an incision in the skin above where the graft is needed. He or she will then shape the donated bone to fit the area. The graft will be held in place using various pins, plates, or screws.

The present invention provides a new and improved type of bone graft and a method of manufacturing the graft to facilitate improved implantation techniques.

SUMMARY OF THE INVENTION

The present invention relates to a fenestrated bone graft and a method of preparing cortical bone in thin strips then fully demineralizing it to give it formed flexibility and then creating fenestrations in the cortical bone in a fashion similar to but not identical to skin grafts.

The advantage of this new allograft is it provides a unique way to develop ingrowth through the fenestrations. The strips can be cut up to 30 cm so they can be used for lateral lumbar fusions or even multiple fusions in the thoracic and lumbosacral spine. The graft can also be rolled into a construct that can be used inside of a cage. The flexibility also allows for the ability to create different shapes such as a tube or a basket that can contain either allogeneric or autogeneric bone graft material with or without stem cells. The fenestrated bone graft is relatively inexpensive and easily scaled. The fenestrated bone graft is a device in which there are created fenestrations which allow for the use bone sutures, suture material made from the same bone that can be used to weave the openings in the fenestrated graft to create a variety of shapes like a cylinder, a basket, a wedge or a roll.

Preferably, a fenestrated cortical graft has an allograft bone structure. The allograft bone structure has an exterior or outer surface and an interior or inner surface. The structure is fenestrated with a plurality of pores or openings extending through from the exterior or outer surface to the interior or inner surface to form open passages. The allograft bone structure can be formed as a flat sheet. Alternatively, the allograft can be formed as a tubular or cylindrical shaped graft. The allograft bone structure is preferably made pliable. The pliable allograft bone structure is conformable to flex about the surface of a damaged bone to provide a fenestrated cortical bone graft.

DEFINITIONS

As used herein and in the claims:

"BMA" refers to Bone Marrow Aspiration, a technique used to obtain the blood-forming portion (marrow) of the inner core of bone for examination in the laboratory or for transplantation.

"Costal cartilage" refers to the cartilages that connect the sternum and the ends of the ribs; its elasticity allows the chest to move in respiration.

Demineralized bone matrix (DBM) is an osteoconductive and osteoinductive commercial biomaterial and approved medical device used in bone defects with a long track record of clinical use in diverse forms. True to its name and as an acid-extracted organic matrix from human bone sources, DBM retains much of the proteinaceous components native to bone, with small amounts of calcium-based solids, inorganic phosphates and some trace cell debris. Many of DBM's proteinaceous components (e.g., growth factors) are known to be potent osteogenic agents. Commercially sourced as putty, paste, sheets and flexible pieces, DBM provides a degradable matrix facilitating endogenous release of these compounds to the bone wound sites where it is surgically placed to fill bone defects, inducing new bone formation and accelerating healing. Given DBM's long clinical track record and commercial accessibility in standard forms and sources, opportunities to further develop and validate DBM as a versatile bone biomaterial in orthopedic repair and regenerative medicine contexts are attractive.

The term "Fenestration" means openings in the walls of a structure.

BRIEF DESCRIPTION OF THE DRAWINGS

The invention will be described by way of example and with reference to the accompanying drawings in which.

DETAILED DESCRIPTION OF THE INVENTION

Figure 2:
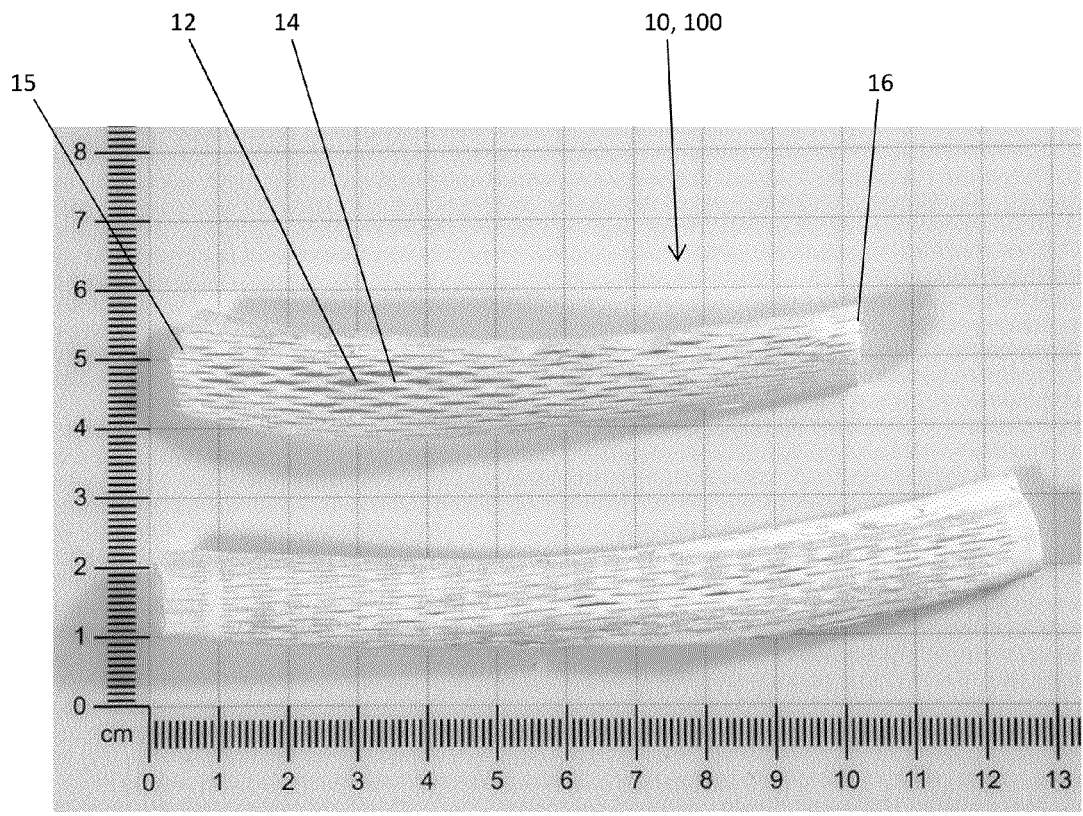
FIG. 2 shows Rib with fenestrations. Clinical indications, cranio and maxillofacial surgery, spinal cage filler (can add micronized bone, dBM, MIAMI cells) to intact center.
Figure 3:
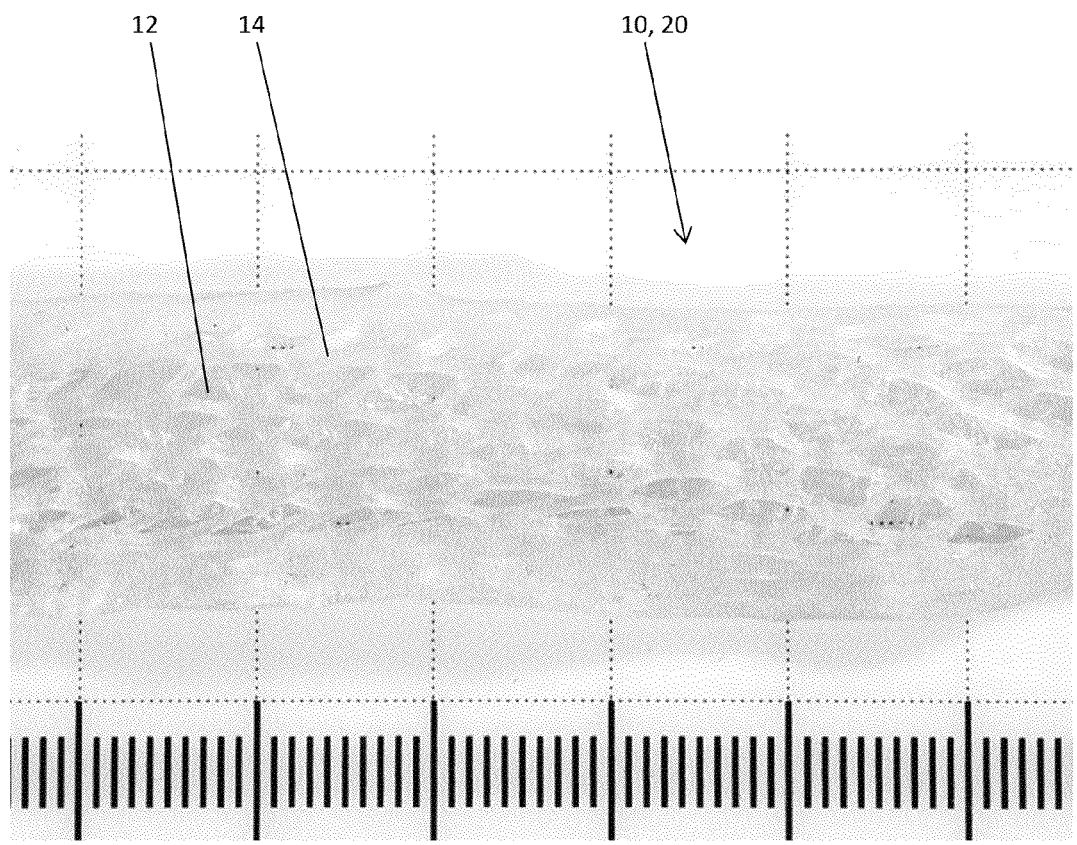
FIG. 3 shows Demineralized rib; higher power magnification demonstrating fenestrations and cortical architecture.

As shown in FIGS. 2 and 3, the original concept of fenestrating demineralized cortical bone was developed in the rib 100 and the rib 100 was an ideal graft because it can essentially be demineralized and creates a large wide flat surface. After removal of the minimal cancellous center, the rib 100 is passed through a press with cutting or punch blades that create fenestrations or openings 12 bounded by interconnected bone struts 14 that gave the fenestrated bone graft 10 a porosity as well as stretchability and flexibility to fit into relatively defined spaces. The actual processing of the rib graft was done aseptically and used no alcohols, peroxides or decontamination steps in its recovery. In doing so, the clinicians removed all of the costal cartilage that they used for other applications and distribution. They cut the rib 100 at ends 15, 16 into relatively long segments at least greater than 8 cm. Following that, they treated the graft for a predetermined time in 1N HCL (one normal hydrochloric acid) (20-50 parts/gram) ranging from approximately 1-3 hours continuously inspecting the graft rigidity. Once they were satisfied with the texture and flexibility of the graft 10 they washed it in a washing solution of Phosphate buffered saline approximately 20 minutes. Then they cut the rib 100 longitudinally to maintain its cylindrical configuration. This cut along the length allowed for either using the graft as a flat construct or it could maintain the graft 10 in a cylinder. The fenestration portion of the graft 10 is cut into the rib 100 and created using an in-house made bone cutter. Once the fenestrations or openings 12 were made in the graft 10, the graft 10 was freeze dried using an overnight cycle and then packaged sterilely for clinical use in a peel pouch. Following the removal of the graft 10 from the plastic peel pouch it can be reconstituted in saline or lactated ringers with or without antibiotics for clinical applications. The graft 10 could be refolded into a cylindrical configuration and filled with either autologous or allogenic bone graft with or without stem cells moreover the graft 10 could be rolled or folded into a confined space such as a cage or rolled into a cylinder where it could be used for the application of satisfying a short close open segment defect. The graft 10 could also be onlaid into a vascularized myo-osseous pouch for the purpose of long segment fusions in the spine, the thoracic or lumbosacral spine.

Figure 1:
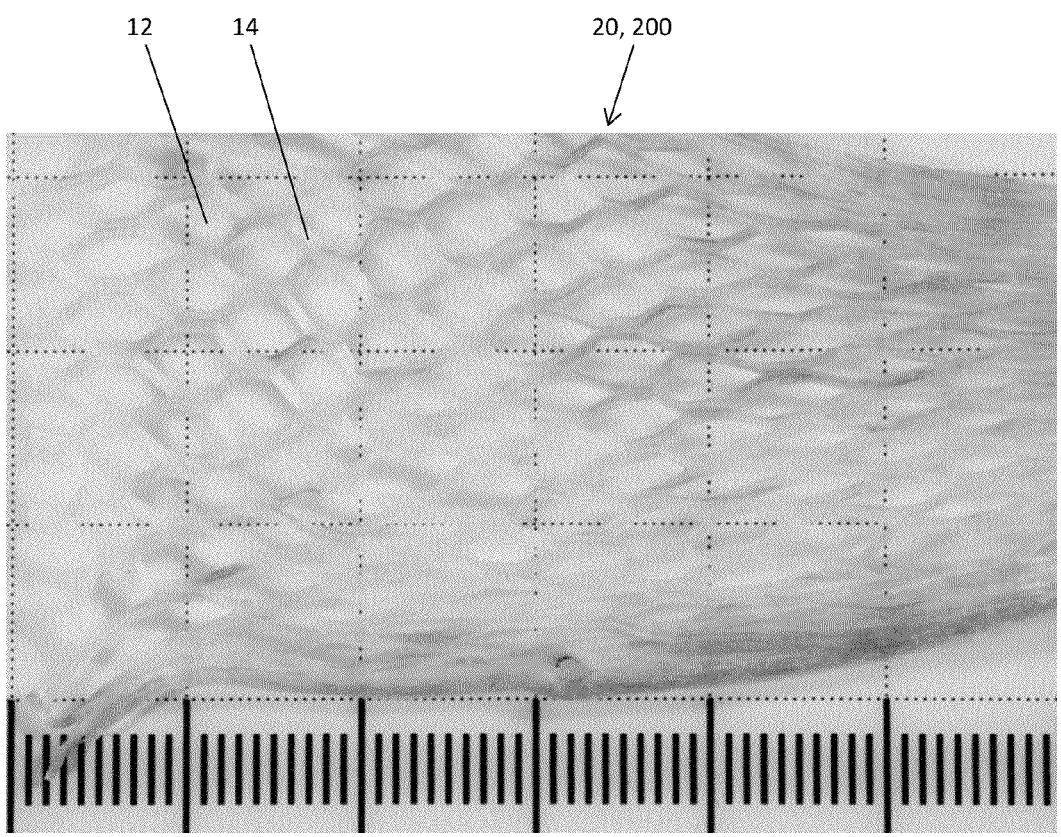
FIG. 1 shows 15-20 cm cortical demineralized graft with fenestrations, Freeze dried. Clinical usage for long segment fusion, segmental defects as a wraparound intramedullary implant.
Figure 4:
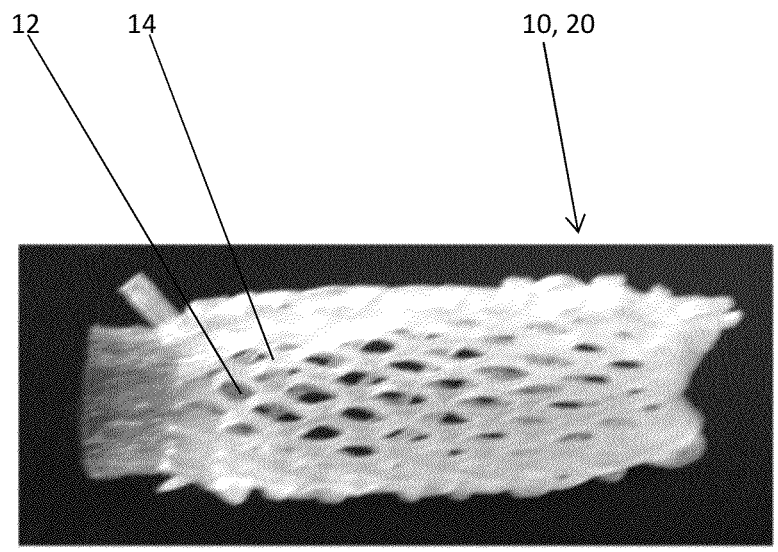
FIG. 4 shows a fenestrated graft strip formed into a basket shape.
Figure 5:
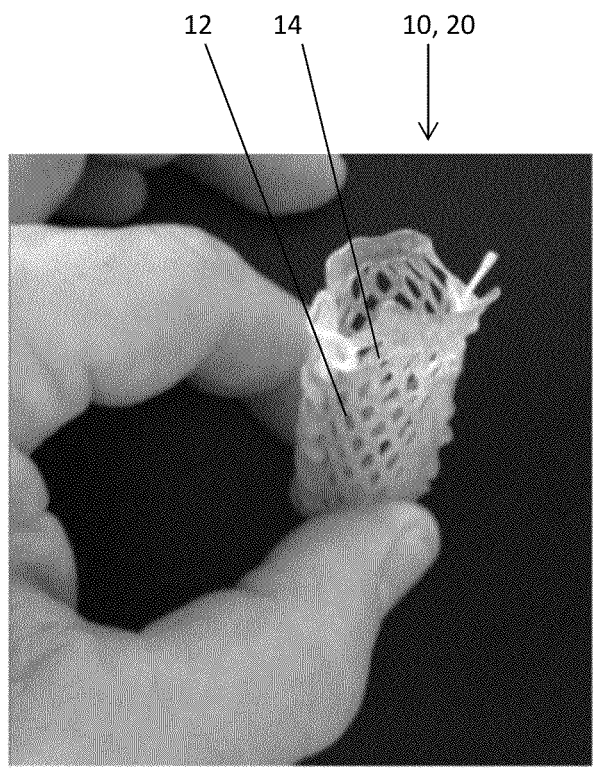
FIG. 5 shows a fenestrated graft strip formed into a basket held by a surgeon.

The tibial graft 20, as shown in FIG. 1, was conceived to create longer segments of bone for very long segment fusions in the case of scoliosis or a multi-segment instability or trauma of the spine. Again the graft 20 was recovered from a tibia 200, in aseptic fashion without the use of peroxides detergents or secondary decontamination steps. Secondary sterilization could however be employed if cultures were positive for non-exclusionary organisms as outlined in FDA guidelines. Aseptic cleaning in the processing state has been reinstituted and the tibia graft 20 was cut on a band saw in a coronal fashion in lengths 10 cm or greater, while the thickness is approximately 0.2 to 1 mm. The graft 20 was then placed in a large graft cylinder and treated with 1N HCL (20-50 parts/gram) for 4-6 hours with continuous inspection to assess the rigidity and texture of the graft 20. Once the appropriate texture was obtained, it was then washed in phosphate buffered saline three separate times for 20 minutes. The graft 20 was then placed on the bone cutter to create the appropriate fenestrations or opening 12 bound by the interconnected bone struts 14 and then the tibia graft 20 was placed in the freeze drier for an overnight cycle. It was then packaged sterilely for clinical use. In using the tibia graft 20, it was removed from the peel pouch and reconstituted in saline or lactated ringers with or without the addition of antibiotics and then depending on the particular application, the tibia graft 20, like the rib graft 10 would be onlaid or folded into a cylinder or a roll or a basket into which particulate graft could be added along with a stem cell. FIGS. 4 and 5 show a basket formed from fenestrated graft 10, 20 strip folded over and laced or woven together to form the basket shape. So the indications for this graft 20 are felt to be long segment fusion such as scoliosis, multi-level and trauma as well as maxillofacial surgery, surgery involving defects in cranial pulp, or long segment defects as well as any other defect.

FIG. 1 is essentially showing a portion of a 20 cm long fenestrated bone graft 20 that was derived from the tibia 200. It is freeze dried and this is done after the fenestrations 12 were created in the graft after it was fully demineralized. Once this fenestrated bone graft 20 is hydrated it resumes its pliable shape and can be formed into several alterations that can retain smaller bone particulate graft and stem cells.

FIG. 2 shows a cylindrical graft 10 made from rib 100. One notes that the fenestrations 12 are created by not having to longitudinally section the rib 100, but using a more robust cut to create fenestrations 12 throughout the graft 10. This is a very interesting graft because it can be filled with allograft bone particulate graft or dbm or stem cells or a combination thereof and can be sewn or restricted above and below at ends 15, 16 of the rib graft 10. This construct can be used to fill a cage construct or potentially to augment a segmental defect or to satisfy a defect in the portion of a long bone or a strip in a pelvis.

FIG. 3 is a higher power magnification showing the morphologic changes that are created in the demineralized cortical bone following fenestration. One notes the uniformity and openness of porous bone structure and the intervening connective strut structure 14 of cortical bone.

The desired texture is a surface related property that has to do with the pliability and stretchability of the grafts 10, 20 themselves. It has to be sufficiently demineralized to have the flexibility which allows creating a variety of different shapes. If too stiff, obviously it can't create these shapes, if demineralized it too much it loses some of the inductivity that is inherent in demineralized bone.

The cut openings 12 or fenestrations 12 are made with a punch press. As shown, these openings 12 are oblong. One can make the openings 12 any size desired. To entrap bone particles calls for pore sizes that are small. This will restrict micronized bone and one could see that these are grafts 10 or 20 formed as strips having the actual pore size about 3 mm long and 1.5 mm wide for the fenestrations 12. The bone connections or struts 14 or strut networks formed are about 1 mm or less in diameter, width or thickness 0.8 to 1.2 mm, at the connective portions, about double that. The actual sizes of the fenestrations 12 can vary in a range from fractions of a millimeter to several millimeters depending on the graft application, 0.2 mm to 5 mm.

This bone graft 10 or 20 could be used as a spacer in the mid-foot and or the fore foot, because of its pliability.

Figure 6:
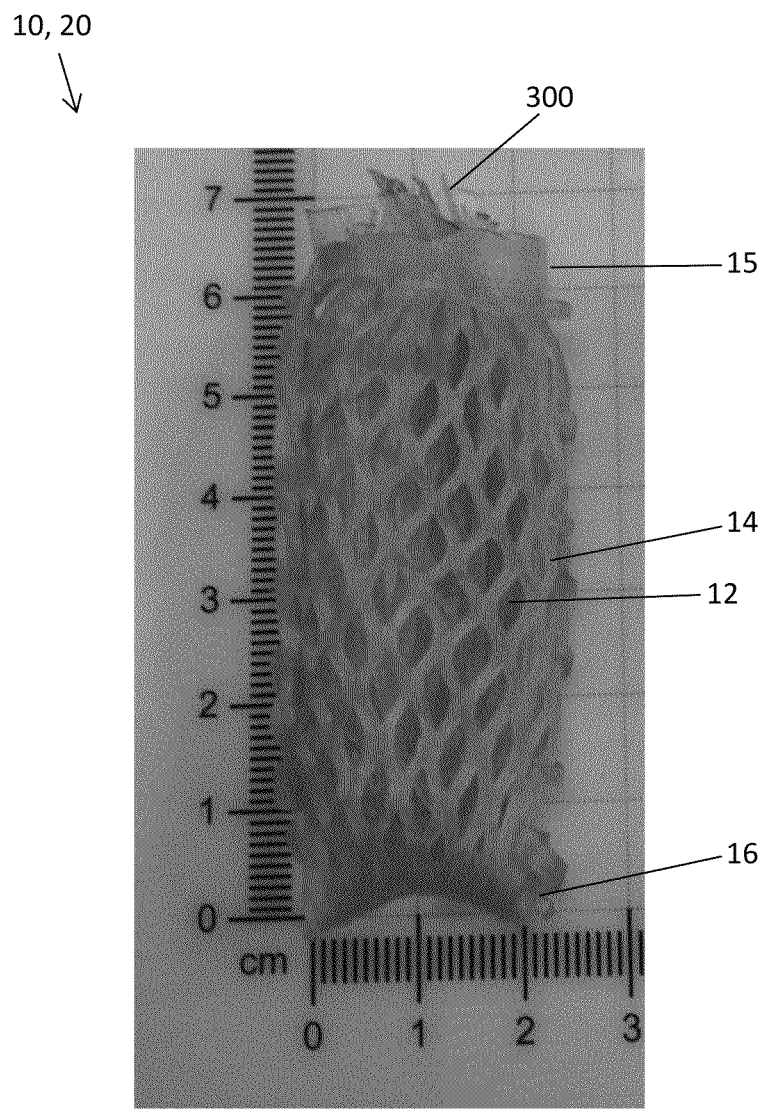
FIG. 6 shows a fenestrated graft strip formed as a pouch or pillow stuffed with a biologic material or stuffing to promote new bone growth.

With reference to FIG. 6, the allograft bone structure 10, 20 can be made in the form of a pouch or pillow 10, 20. It uses 100% human demineralized cortical sheet. The pillow 10, 20 is meshed, perforated bone with fibrous cortical cancellous stuffing 300. The stuffing 300 can be cancellous bone material, autologous or allogenic bone graft, with or without stem cells, allograft bone particulate graft or dbm or stem cells, BMA or any combination thereof. The pillow ends 15, 16 can be sutured. Cortical sheet is machine stamped for consistency in the open area as previously discussed. It has flexible handling characteristics with osteoconductive and osteoinductive properties. It is easy to handle and deliver, is pre-configured implant sized to the specific procedure and it aims to solve the common problems of graft site migration and the ability to visualize the implant post-surgery. It can be made available in multiple lengths. It has a 5 year shelf life at room-temperature storage and can be conveniently distributed in packs of 2. As shown, the demineralized cortical meshed perforated "pillows" 10, 20 can be processed from donated human bone utilizing the previously discussed demineralization technology; the grafts are flexible and feature osteoinductive and osteoconductive properties. When combined with BMA, it provides all of the necessary elements for bone regeneration. It is designed for posterolateral and cervical spine surgery applications including single- and multi-level fusions, as well as deformity procedures. It can be distributed in packs of 2 to provide fusion material for both sides of the spine, thus minimizing the number of boxes to open during procedures. It can be provided in various sizes, for example: 20 mm×50 mm (2) for Posterolateral applications; 10 mm×100 mm (2) for Spinal Deformity; and 10 mm×50 mm (2) for Posterior Cervical applications.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A fenestrated cortical graft comprises:
an allograft bone structure, the allograft bone structure having an exterior or outer surface and an interior or inner surface, the structure being fenestrated with a plurality of pores or openings extending through from the exterior or outer surface to the interior or inner surface to form open passages and the allograft bone structure is formed as a tubular or cylindrical shaped graft, the tubular or cylindrical shaped graft has a pair of ends, wherein both of the ends are sutured or woven closed.

2. The fenestrated cortical graft of claim 1 wherein the allograft bone structure is made pliable.

3. The fenestrated cortical graft of claim 2 wherein the allograft bone structure is conformable to flex about the surface of a damaged bone to provide a fenestrated cortical bone graft.

4. The fenestrated cortical graft of claim 1 wherein the bone structure is from a rib.

5. The fenestrated cortical graft of claim 1 wherein the bone structure is from a tibia.

6. The fenestrated cortical graft of claim 1 wherein the bone allograft structure has a thickness of 0.2 mm to 1 mm.

7. The fenestrated cortical graft of claim 6 wherein the openings are sized to be in the range of 0.2 mm to 5 mm.

8. The fenestrated cortical graft of claim 7 wherein the structure form has struts in a size of 0.8 mm to 1.2 mm.

9. The fenestrated cortical graft of claim 8 wherein at the connective portions of the strut the size doubles.

10. The fenestrated cortical graft of claim 1 wherein when both ends are closed, the allograft bone structure forms a pouch.

11. The fenestrated cortical graft of claim 1 wherein the pouch is filled with a stuffing made with one or more of cancellous bone material, autologous or allogenic bone graft, with or without stem cells, allograft bone particulate graft or dbm or stem cells, BMA or any combination thereof.

* * * * *